United States Patent [19]

Tabak et al.

[11] 4,236,996
[45] * Dec. 2, 1980

[54] XYLENE ISOMERIZATION

[75] Inventors: Samuel A. Tabak, Wenonah; Roger A. Morrison, Deptford, both of N.J.

[73] Assignee: Mobil Oil Corporation, New York, N.Y.

[*] Notice: The portion of the term of this patent subsequent to Feb. 12, 1997, has been disclaimed.

[21] Appl. No.: 43,395

[22] Filed: May 25, 1979

Related U.S. Application Data

[63] Continuation-in-part of Ser. No. 914,645, Jun. 12, 1978, Pat. No. 4,188,282.

[51] Int. Cl.³ .................................................. C10G 35/04
[52] U.S. Cl. .................................... 208/134; 585/481; 585/486; 585/489
[58] Field of Search ............. 585/486, 481, 489; 208/134

[56] References Cited

U.S. PATENT DOCUMENTS

| | | | |
|---|---|---|---|
| 3,856,871 | 12/1974 | Haag et al. | 585/481 |
| 3,856,872 | 12/1974 | Morrison | 585/481 |
| 3,856,873 | 12/1974 | Burress | 585/481 |

*Primary Examiner*—C. Davis
*Attorney, Agent, or Firm*—Charles A. Huggett; Raymond W. Barclay

[57] ABSTRACT

Isomerization of xylenes in admixture with ethylbenzene by contact with a zeolite catalyst such as ZSM-5 is improved by use of zeolite which has been steamed at high temperature to reduce activity, the reaction being at a temperature above about 700° F. At these conditions, conversion of ethylbenzene follows a different reaction path which permits high conversion of ethylbenzene to benzene without loss of xylenes of disproportionation.

10 Claims, 1 Drawing Figure

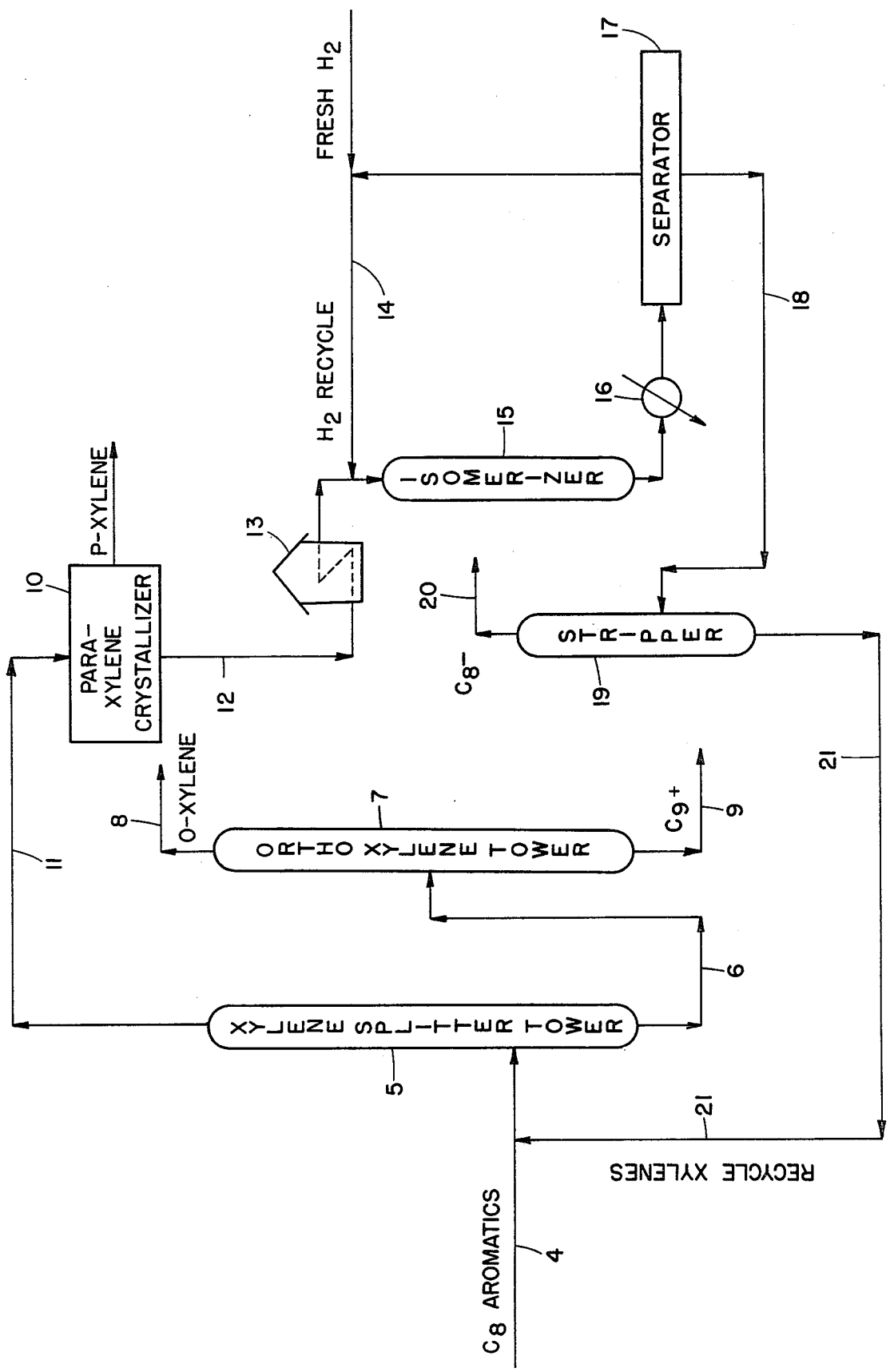

XYLENE ISOMERIZATION

CROSS-REFERENCE TO RELATED APPLICATIONS

This application is a continuation in part of copending application Ser. No. 914,645, filed June 12, 1978 now U.S. Pat. No. 4,188,282.

BACKGROUND OF THE INVENTION

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York 1961). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually be selective solvent extraction. The $C_8$ aromatics in such mixtures and their properties are:

|  | Freezing Point °F. | Boiling Point °F. |
| --- | --- | --- |
| Ethyl benzene | −139.0 | 277.1 |
| P-xylene | 55.9 | 281.0 |
| M-xylene | −54.2 | 282.4 |
| O-xylene | −13.3 | 292.0 |

Principal sources are catalytically reformed naphthas and pyrolysis distillates. The $C_8$ aromatic fractions from these sources vary quite widely in composition but will usually be in the range 10 to 32 wt.% ethylbenzene with the balance, xylenes, being divided approximately 50 wt.% meta, and 25 wt.% each of para and ortho.

Individual isomer products may be separated from the naturally occurring mixtures by appropriate physical methods. Ethylbenzene may be separated by fractional distillation although this is a costly operation. Ortho-xylene may be selected by fractional distillation and is so produced commercially. Para-xylene is separated from the mixed isomers by fractional crystallization.

As commercial use of para and ortho-xylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene or xylenes separation process. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethylbenzene introduced with charge to the recovery/isomerization "loop". That compound, normally present in eight carbon atom aromatic fractions, will accumulate in the loop unless excluded from the charge or converted by some reaction in the loop to products which are separable from xylenes by means tolerable in the loop. Ethylbenzene can be separated from the xylenes of boiling point near that of ethylbenzene by extremely expensive "superfractionation". This capital and operating expense cannot be tolerated in the loop where the high recycle rate would require an extremely large distillation unit for the purpose. It is a usual adjunct of low pressure, low temperature isomerization as a charge preparation facility in which ethylbenzene is separated from the virgin $C_8$ aromatic fraction before introduction to the loop.

Other isomerization processes operate at higher pressure and temperature, usually under hydrogen pressure in the presence of catalysts which convert ethylbenzene to products readily separated by relatively simple distillation in the loop, which distillation is needed in any event to separate by-products of xylene isomerization from the recycle stream. For example, the Octafining catalyst of platinum on a silica-alumina composite exhibits the dual functions of hydrogenation/dehydrogenation and isomerization.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethylene and benzene and hydrocracking of the alkyl cyclohexanes.

The rate of ethylbenzene approach to equilibrium concentration in a $C_8$ aromatic mixture is related to effective contact time. Hydrogen partial pressure has a very significant effect on ethylbenzene approach to equilibrium. Temperature change within the range of Octafining conditions (830° to 900° F.) has but a very small effect on ethylbenzene approach to equilibrium.

Concurrent loss of ethylbenzene to other molecular weight products relates to percent approach to equilibrium. Products formed from ethylbenzene include $C_6^+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than the reaction of ethylbenzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethylbenzene has been found responsible for a relatively rapid decline in catalyst activity and this effect is proportional to its concentration in a $C_8$ aromatic feed mixture. It has been possible then to relate catalyst stability (or loss in activity) to feed composition (ethylbenzene content and hydrogen recycle ratio) so that for any $C_8$ aromatic feed, desired xylene products can be made with a selected suitably long catalyst use cycle.

A different approach to conversion of ethylbenzene is described in Morrison U.S. Pat. No. 3,856,872, dated Dec. 24, 1974. Over an active acid catalyst typified by zeolite ZSM-5, ethylbenzene disproportionates to benzene and diethylbenzene which are readily separated from xylenes by the distillation equipment needed in the loop to remove by-products. It is recognized that rate of disproportionation of ethylbenzene is related to the rate of conversion of xylenes to other compounds, e.g. by disproportionation. See also Burress U.S. Pat. No. 3,856,873 which also describes reaction of $C_8$ aromatics over ZSM-5 and shows effects of various temperatures up to 950° F. in the absence of metal co-catalyst and in the absence of hydrogen.

In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further advance in the art is described in copending applications of the present applicants directed to various techniques for reducing acid activity of zeolite ZSM-5 catalysts for xylene isomerization concurrently with ethylbenzene conversion at temperatures upwards of 800° F. One such copending application is Ser. No. 912,681, filed June 5, 1978, now U.S. Pat. No. 4,163,028, which discloses xylene isomerization and ethylbenzene conversion at high temperature with ZSM-5 of very high silica/alumina ratio whereby the acid activity is reduced.

The inventions of those copending applications and the present invention are predicated on discovery of combinations of catalyst and operating conditions which decouples ethylbenzene conversion from xylene loss in a xylene isomerization reaction, thus permitting feed of $C_8$ fractions which contain ethylbenzene without sacrifice of xylenes to conditions which will promote adequate conversion of ethylbenzene.

DESCRIPTION OF DRAWING

A plant suited to practice of the invention is illustrated as a diagrammatic flow-sheet in the single FIGURE of the annexed drawing.

SUMMARY OF THE INVENTION

The process of the invention utilizes a low acidity zeolite catalyst. The low acidity zeolite is obtained by steaming for one or more hours at temperatures upwards of 700° F., the time, pressure and temperature being interrelated such that less time is required at higher temperatures and/or pressures. The catalyst may contain metals such as platinum or nickel. In using this less active catalyst the temperature is raised to above 700° F. to attain xylene isomerization, preferably to 800° F. or higher. At these temperatures, ethylbenzene reacts primarily via dealkylation to benzene and ethane (or ethylene in the absence of hydrogen and hydrogenation co-catalyst) rather than via disproportionation to benzene and diethylbenzene and hence is strongly decoupled from the catalyst acid function. Since ethylbenzene conversion is less dependent on the acid function, a lower acidity catalyst can be used to perform the relatively easy xylene isomerization, and the amount of xylenes disproportionated is eliminated. The reduction of xylene losses is important because about 75% of the xylene stream is recycled in the loop resulting in an ultimate xylene loss of 6-10 Wt.% by previous processes.

Since most of the ethylbenzene goes to benzene instead of benzene plus diethyl benzenes, the product quality of the new process is better than that of prior practices.

The new process also allows greater flexibility with respect to charge stock. Since ethylbenzene conversion is relatively independent of isomerization; high ethylbenzene containing charge stocks can be processed, which means that charge stocks from thermal crackers (about 30 wt.% ethylbenzene) can be used as well as conventional stocks from reformers. In addition, dealkylation of $C_2+$ alkyl groups is favored since the temperature is above 800° F. As a result, paraffins in the charge stock will not alkylate the aromatic rings eliminating xylene loss via this mechanism. Thus, the new process can process paraffins in the charge by cracking them to lighter paraffins eliminating the need for Udex Extraction. Finally, a small portion of the cracked fragments are recombined to form new aromatic rings which results in a net increase of aromatic rings.

DESCRIPTION OF SPECIFIC EMBODIMENTS

The foregoing objects and advantages are obtained in a plant corresponding to the flow sheet in the annexed drawing. The charge introduced by line 4 is a mixture of eight carbon atom alkyl aromatics, namely ethylbenzene and the three xylene isomers. Such charge stocks are derived from catalytic reformates, pyrolysis gasoline, etc. by distillation and solvent extraction to separate aromatic compounds from aliphatics. The present process has the ability, unique among xylene isomerication processes, of converting paraffins, olefins and the like which are separated by the normal distillation facilities of an isomerization loop. This process is therefore capable of accepting charge materials which contain substantial quantities (say up to 15%) of aliphatic hydrocarbons. Other sources for production of xylenes include toluene disproportionation and methylation of toluene. These charge stocks contain little or no ethylbenzene and therefore cannot take advantage of the novel ethylbenzene conversion feature of the invention. However, these are acceptable charge stocks alone or in combination with fractions which contain ethylbenzene. Such charge stock passes by line 4 to a xylene splitter column 5. The bottoms from the xylene splitter, constituted by o-xylene and $C_9$ aromatics passes by line 6 to the o-xylene tower 7 from which o-xylene is taken overhead at line 8 and heavy ends are removed by line 9. The overhead from xylene splitter column 5 is transferred to conventional crystallization separation 10 through line 11. The crystallizer may operate in the manner described in Machell et al., U.S. Pat. No. 3,662,013 dated May 9, 1972.

Because it's melting point is much higher than that of the other $C_8$ aromatics, p-xylene is readily separated in the crystallizer after refrigeration of the stream and a xylene mixture lean in p-xylene is transferred to an isomerization unit through line 12. The isomerization charge passes through a heater 13, is admixed with hydrogen admitted through line 14 and the mixture is introduced to the reactor 15 operated in a manner presently to be described.

Isomerized product from reactor 15 is cooled in heat exchanger 16 and passes to a high pressure separator 17 from which separated hydrogen can be recycled in the process. The liquid product of the isomerization passes by line 18 to a stripper 19 from which light ends are passed overhead by line 20. The remaining liquid product constituted by $C_8+$ hydrocarbons is recycled in the system by line 21 to the inlet of xylene stripper column 5.

It will be seen that the system is adapted to produce maximum quantities of p-xylene from a mixed $C_8$ aromatic feed containing all of the xylene isomers plus ethylbenzene. The key to efficient operation for that purpose is in the isomerizer which takes crystallizer effluent lean in p-xylene and converts the other xylene isomers in part to p-xylene for further recovery at the crystallizer.

The reactor 15 contains a crystalline aluminosilicate (zeolite) catalyst of relatively low acid activity by reason of its treatment with steam at high temperatures. That catalyst, which is preferably combined with a metal from Group VIII of the Periodic Table promotes a reaction course which is unique at temperatures upwards of 700° F. At 800° F., ethylbenzene in the charge is selectively cracked to benzene and ethane at little or no conversion of xylenes to compounds other than xylenes, e.g. by disproportionation. The two conversions are, as noted above, decoupled such that, for the first time, reaction severity is not a compromise to achieve effective ethylbenzene conversion at "acceptable" loss of xylene. This characteristic of the process renders unnecessary the preliminary distillation to separate at least some of the ethylbenzene from the feed stream as practiced in prior processes. It has been further found that the present process has capability to convert paraffin hydrocarbons. This makes it possible to dispense with the expensive extraction step conventionally applied to the $C_8$ aromatic fraction of catalytically reformed naphthas in the manufacture and recovery of xylenes. In taking advantage of this feature, the feed stream at line 4 will contain the $C_8$ aromatics of a reformate or the like together with the paraffins of like boiling range, mostly nonanes. The paraffins in the charge are hydrocracked to lighter paraffins, including ethane, which will come off separator 17 with the recycle hydrogen in much greater quantity than that resulting from conversion of ethylbenzene. This requires modification of the usual techniques for maintaining concentration of the recycle hydrogen stream by withdrawal of a drag stream, not shown in the drawing.

The flow sheet of the drawing contemplates separate recovery of o-xylene. It will be immediately apparent that this isomer may be recycled in the system in the event o-xylene is not a desired product. In that event, splitter tower 5 is operated to take o-xylene overhead with the other $C_8$ aromatics and take only $C_9+$ as bottoms from tower 5.

Particularly preferred are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination a silica to alumina mole ratio of at least about 12; and a structure providing constrained access to the crystalline free space.

The zeolite will have a silica/alumina ratio greater than 12. The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type of zeolites described freely sorb normal hexane and have a pore dimention greater than about 5 Angstroms. In addition, the structure must provide constrained access to large molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methyl pentane remaining)}}$$

The constraint index approximates the ratio of the cracking rate constants for the two hydrocarbons. Zeolites suitable for the present invention are those having a constraint index in the approximate range of 1 to 12.

| ZEOLITE | C. I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-14 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may effect the constraint index. It will accordingle be understood by those skilled in the art that the constraint index, as utilized herein, while affording a highly useful means for characterizing the zeolites of interest is approximate, taking into consideration the manner of its determination, with probability, in some instances, of compounding variables extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio or high sodium content. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally it is possible (and is usual practice) to activate this type catalyst by base exchange with ammonium salts followed by calcination in air or about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-35, and ZSM-38, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pykometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite may be converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been replaced by another cation may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix mterial, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the neighborhood of about 65 percent by weight of the composite.

As pointed out above, a prior copending application Ser. No. 912,681, filed June 5, 1978, describes a novel method of processing $C_8$ aromatics for isomerization of xylenes and conversion of ethylbenzene. According to that prior application, the reactions are conducted at temperatures of 800° to 1000° F. with a zeolite having a constraint index of 1 to 12 and a very high silica/alumina ratio which may be as high as or higher than 3000. Such catalysts have low acid activity by reason of the small number of sites capable of being rendered protonic by ammonium exchange and calcination.

According to the present invention, like results are obtained with zeolites having constraint indexes in the range of 1 to 12 and abnormally low acid activity by reason of steaming at high temperature which is believed to destroy protonic or acid sites in the zeolite.

The zeolite catalysts to be steamed according to the invention are generally those zeolites of at least 12 silica/alumina ratio and a constraint index of 1 to 12 which, in the acid form, have activity to convert about 30% of the ethylbenzene in a mixture thereof with xylenes under the isomerization conditions of the said Morrison U.S. Pat. No. 3,856,872, say 600°–700° F. The degree of steaming shall be such that reaction temperature must be increased by 50°–100° F. to attain the same ethylbenzene conversion as was observed before steaming. The reaction of the present invention will then be conducted at such elevated temperatures, above 700° F., as to realize about 30% conversion of the ethylbenzene in the charge. As the temperature is further increased to and above about 800° F. the reaction of ethylbenzene shifts from disproportionation to dealkylation.

For purposes of comparison, it is noted that the typical process of the Morrison Patent utilizes a catalyst containing 65% Ni-ZSM-5 ($SiO_2/Al_2O_3=70$) and 35% alumina binder. Employing this catalyst, at approximately 600°–700° F. the process has the following reaction characteristics:

1. ethylbenzene (EB) conversion occurs over the catalyst acid function resulting primarily in disproportionation to benzene and diethylbenzene
2. xylene isomerization occurs over the acid function
3. xylenes are lost over the acid function via disproportionation to toluene and $C_9$ methylbenzenes
4. paraffins cannot be processed because the cracked fragments will alkylate the xylenes which increases xylene loss
5. xylenes are lost over the acid function via transalkylation with ethyl groups from EB conversion Thus the present invention involves using high temperature steam to partially deactivate the catalyst. The deactivation should be conducted to a level such that the process requires a minimum 50° F. rise in operating temperature. Depending on the amount of temperature rise which results from the steam deactivation, different alterations of process behavior are observed. Initially, for cases of light steaming, (i.e., temperature rise of 50° to 100° F.), the xylene loss is seen to decrease about 40% from comparable operation with unsteamed catalyst. Other than the decrease in xylene loss, no significant change in chemistry is observed. However, if the catalyst undergoes a more severe steaming (i.e., temperature rise greater than 200° F.), the process will assume some general characteristics, of the previously described process using high silica/alumina ratio ZSM-5. For this case, not only is xylene loss reduced, but ethylbenzene now reacts primarily by dealkylation to benzene and ethane rather than by disproportionation to benzene and diethylbenzene, thus improving the product quality. In addition, at this temperature, paraffins in the charge stock will not alkylate the aromatic rings eliminating xylene loss via this mechanism. Thus, following a severe steaming, this new process can react paraffins in the charge by cracking them to lighter paraffins eliminating the need for Udex extraction.

A major value of this development is that for existing plants, catalyst steaming can be performed in situ. This can be done by treating the catalyst, in the reactor, with steam at temperatures of about 750° F. or above until the desired level of catalyst deactivation is reached.

This process differs from that of the Morrison Patent in that:
1. it uses a steamed ZSM-5 catalyst, where the steam is used to reduce the catalyst acidity
2. has less xylene losses via alkylation, disproportionation and transalkylation
3. allows existing plants to reduce their xylene losses by in situ steaming of their catalyst
4. if sufficient steaming is performed, this process will assume the general characteristics of high temperature isomerization i.e., can convert paraffin charge stocks, and make benzene from ethylbenzene rather than benzene+diethylbenzene.

These effects are clearly seen in Table 1 reporting three examples which result from a prolonged test in which isomerization was interrupted to steam the catalyst in the reactor. The catalyst was nickel on acid ZSM-5 of 70 silica/alumina ratio in the form of extruded pellets with 35 wt. % alumina binder. Steaming pre-treatment conditions and conditions of reaction are shown for charging a mixture of 0.1% toluene, 14.9% ethylbenzene, 68.6% m-xylene, 9.4% p-xylene, 6.9% o-xylene and 0.1% C9 hydrocarbons. It will be seen that ethylbenzene conversion is held substantially constant by increased temperature as the catalyst is twice deactivated by high temperature steaming. Over these conditions, the degree of isomerization is substantially constant and the xylene loss (by conversion to other compounds) changes dramatically for the better.

TABLE 1

| Effect of in situ steaming of ZSM-5 on xylene isomerization | | | |
|---|---|---|---|
| Example No. | 1 | 2 | 3 |
| Steam Treat | None | | |
| Hours | | 17 | 16 |
| Temperature, °F. | | 800 | 900 |
| Pressure, psig | | 100 | 200 |
| Reaction conditions | | | |
| Time, hours | 3 | 52 | 74 |
| Temp. °F. | 625 | 710 | 870 |
| Pressure, psig | 200 | 200 | 200 |
| WHSV | 5 | 5 | 5 |
| H2/HC | 5 | 5 | 5 |
| Product Dist., wt. % | | | |
| Paraffins | 1.16 | 0.56 | 1.17 |
| Benzene | 2.81 | 2.99 | 3.64 |
| Toluene | 2.12 | 0.44 | 0.50 |
| Ethylbenzene | 9.41 | 9.76 | 9.64 |
| m-xylene | 43.81 | 44.76 | 45.01 |
| p-xylene | 18.32 | 19.36 | 19.38 |
| o-xylene | 17.46 | 18.36 | 19.02 |
| C9+Arom. | 4.41 | 3.79 | 1.64 |
| Wt. % conversion EB | 36.84 | 34.49 | 35.30 |
| Xylene loss, wt. % | 4.81 | 2.42 | 1.49 |
| Mole benzene made | 0.69 | 0.79 | 0.94 |
| Mole EB reacted | | | |

The capability of the process to handle paraffins in the charge at temperatures of 800° F. or above is exemplified by the experimental data in Table 2. The catalyst was 3.9% nickel ZSM-5 extrudate which had been steamed 48 hours at 900° F., 100 psig. For each example, analysis of the charge precedes the column reporting reaction conditions and product distribution.

TABLE 2

| Effect of paraffins in charge to steamed ZSM-5 isomerization catalyst | | | | |
|---|---|---|---|---|
| Example | | 4 | | 5 |
| Temp. °F. | | 810 | | 810 |
| Pressure, psig | | 200 | | 200 |
| WHSV | | 5 | | 5 |
| H2/HC | | 5 | | 5 |
| Time, hours | | 24 | | 48 |
| Product Dist. | | | | |
| C1–C7PAR | | 0.77 | | 6.37 |
| Benzene | Charge | 3.85 | Charge | 6.77 |
| Toluene | 0.1 | 1.22 | | 0.99 |
| C8PAR | | 0.02 | | 0.03 |
| Ethylbenzene | 14.9 | 9.58 | 26.0 | 16.18 |
| m-xylene | 68.6 | 45.37 | 50.1 | 32.20 |
| p-xylene | 9.4 | 19.45 | 6.9 | 14.12 |
| o-xylene | 6.9 | 18.18 | 5.0 | 13.33 |
| C9+PAR | 0.1 | 0.00 | 11.9 | 6.78 |
| C9+Arom. | | 1.57 | 0.9 | 3.24 |
| Wt. % Conversion EB | | 37.70 | | 37.76 |
| Wt. % Conversion C9+ | | | | 43.02 |
| Xylene loss | | 1.90 | | 2.35 |

The process of this invention is suited to practice in existing facilities of different types, since the catalyst operates effectively at low pressure, e.g. atmospheric, in the absence of added hydrogen or at high pressure in the presence of hydrogen, e.g. Octafining conditions. In the latter case, the catalyst will be used in combination with a metal such as nickel or platinum having activity for hydrogenation/dehydrogenation reactions.

We claim:

1. In a process for isomerizing the xylene content of a charge mixture of eight carbon atom aromatic hydrocarbon compounds which mixture contains xylene and ethylbenzene by contact at conversion conditions with a catalyst comprising a zeolite having a silica/alumina ratio greater than 12 and a constraint index of 1 to 12, the improvement which comprises using as said catalyst a steamed zeolite and maintaining a conversion temperature of about 700° F. to about 1000° F.; said zeolite having been steamed prior to said contact under a temperature and pressure and for a period of time such that the steamed zeolite requires an increased reaction temperature of at least 50° F. to equal the ethylbenzene conversion by the unsteamed zeolite.

2. A process according to claim 1 wherein said zeolite is ZSM-5.

3. A process according to claim 1 wherein said catalyst also comprises a metal of Group VIII of the Periodic Table.

4. A process according to claim 3 wherein said zeolite is ZSM-5.

5. A process according to claim 3 wherein said charge mixture is admixed with hydrogen.

6. A process according to claim 5 wherein said zeolite is ZSM-5.

7. A process according to claim 1 wherein the reaction temperature is 700°–800° F.

8. A process according to claim 7 resulting in conversion of ethylbenzene to benzene at substantially no loss of xylene in the product as compared to the charge.

9. A process according to claim 7 wherein the said charge mixture contains paraffin hydrocarbons.

10. A process according to claim 1 wherein the said charge mixture consists essentially of aromatic hydrocarbons.

* * * * *

UNITED STATES PATENT AND TRADEMARK OFFICE
CERTIFICATE OF CORRECTION

PATENT NO. : 4,236,996
DATED : December 2, 1980
INVENTOR(S) : Samuel A. Tabak et al.

It is certified that error appears in the above—identified patent and that said Letters Patent is hereby corrected as shown below:

Column 7, line 12, add -- Constraint Index (CI) values for some typical zeolites are: --

Column 9, line 53, "mterial" should read -- material --.

Signed and Sealed this

Twenty-third Day of June 1981

[SEAL]

Attest:

RENE D. TEGTMEYER

Attesting Officer     Acting Commissioner of Patents and Trademarks